United States Patent [19]

Bukamier

[11] 4,128,468
[45] Dec. 5, 1978

[54] ELECTRODE STRUCTURES

[76] Inventor: Gary L. Bukamier, 4341 Eureka, Yorba Linda, Calif. 92686

[21] Appl. No.: 866,283

[22] Filed: Jan. 3, 1978

[51] Int. Cl.² ............................................. G01N 27/30
[52] U.S. Cl. .............................. 204/195 F; 204/195 G
[58] Field of Search ............. 204/195 F, 195 G, 1 H, 204/195 R, 195 B; 324/30 R, 29

[56] References Cited

U.S. PATENT DOCUMENTS

| 3,741,884 | 6/1973 | Deushane et al. | 204/195 F |
| 3,957,612 | 5/1976 | Niedrach et al. | 204/195 M |
| 4,053,382 | 10/1977 | Maruyama et al. | 204/195 F |

Primary Examiner—G. L. Kaplan
Attorney, Agent, or Firm—Grover A. Frater

[57] ABSTRACT

An ion sensitive electrode structure employing concentrically arranged inner and outer tubular members employs a porous plug to seal the annular space between the tubular members and to enable formation of a salt bridge. The plug is made of porous Teflon and, in preferred form, it is combined with an encompassing sealing annulus which seals an annular space between the outer wall of the plug and the inner wall of the outer tubular member. In a form preferred for some applications, two such plugs and sealing annulus' are employed and are held separated by a spacer.

9 Claims, 7 Drawing Figures

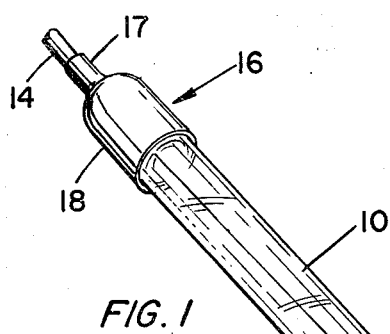
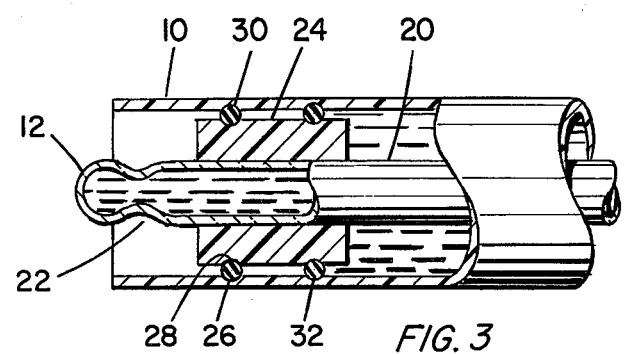
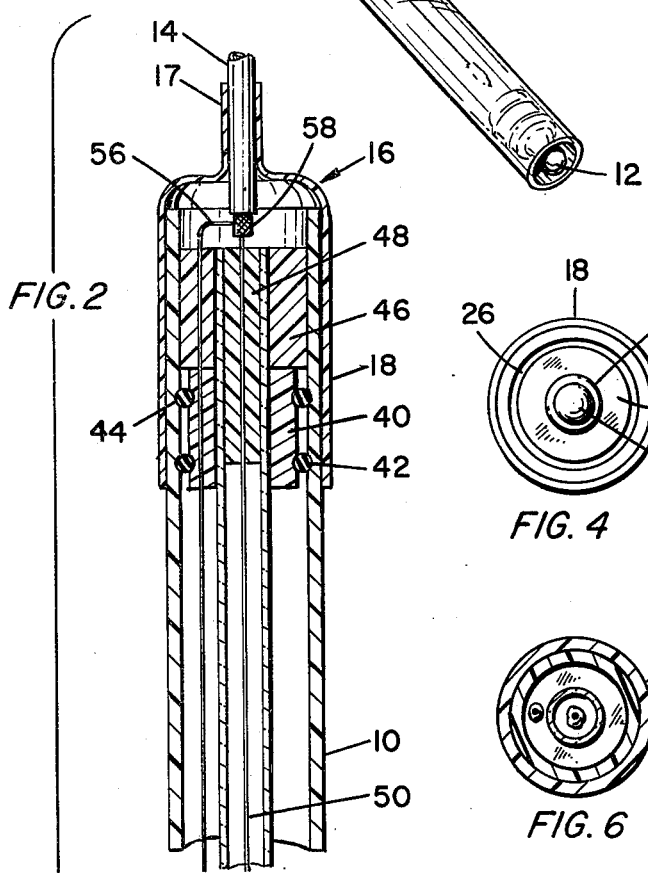
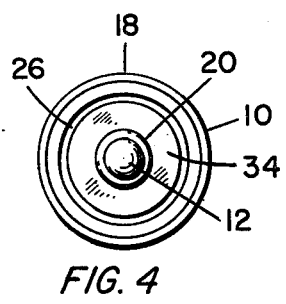
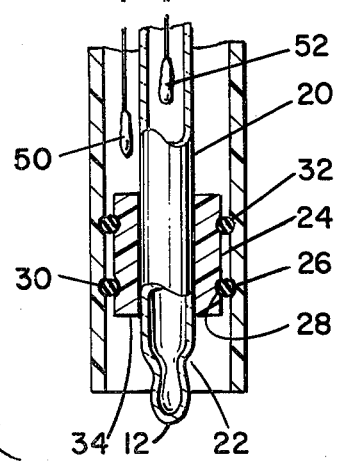
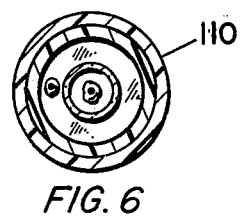
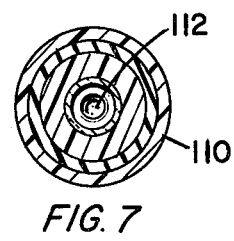

ELECTRODE STRUCTURES

This invention relates to improvements in the physical structure of ion sensitive electrodes. It relates in particular to improvements in the class of electrodes which employ concentrically arranged inner and outer tubes and a salt bridge in a combined sensor and reference half-cell unit.

BACKGROUND OF THE INVENTION

Measurements to discover the presence and the concentration of ions in liquids may be accomplished electrically. A sensor is employed in which there is a conduction of electricity in proportion to the kind and concentration of ions. The amount of that conduction is measured in a conventional instrument, usually a very high input impedance voltmeter. The electrical circuit extends through the junction of several dissimilar materials as it proceeds from the liquid through the sensor to the metallic conductors of the measuring instrument and back to the liquid. A junction potential appears at each juncture of dissimilar materials the magnitude of which may approach or exceed the potentials that are generated at the sensor in its measurement of ion concentration. In that circumstance, the junction potentials must be known or the circuit rearranged to include equal but opposite junction potentials.

One of the most satisfactory means that has been devised to deal with undesired junction potentials is to employ a pair of half-cells in series with the sensing element and with one another in making the physical connection from the sampled liquid to the metallic conductors of the measuring instrument. The metal conductor of the instrument, ordinarily copper, is connected to a metal, such as silver, whose salt, such, for example, as silver chloride, readily exchanges ions with a dissolved salt with which it shares a common ion, such, for example, as potassium chloride. The potassium chloride is placed in physical contact with the sample material in which ion concentration is to be measured. The ion sensor also is placed in contact with the sample material. The electrical measuring circuit is completed from the sensor back to the instrument by placing the sensor in contact with a quantity of the same dissolved salt which contacts a quantity of the same metal salt which contact a conductor made of the metal of that same metal salt which, in turn, is connected to the metal conductors of the instrument. That arrangement includes several pairs of oppositely polarized dissimilar junctions, and it provides a means for accounting for junction potentials. However, that circuit imposes the requirement for a structural arrangement in which two quantities of salt solution can be retained while contacting the metal salt on one hand and the sample liquid and the sensor on the other hand. The physical problem of contacting the salt solution and the sensor is not very great in most cases because most sensors are formed of solid materials which can form a wall of a salt solution container. An example is the glass electrode employed in measuring pH where the pH sensitive glass forms a wall of a glass container in which the salt solution is disposed.

Finding a suitable structure which will retain a quantity of salt solution while permitting physical contact with the sample solution, without contamination or loss of one to the other, is a more difficult problem. Such structures do exist. They are called "salt bridges" in the art. There are, in fact, a wide range and variety of salt bridge structures. The great number of such structures, and the fact that the search for more structures continues, is evidence of the fact that finding a suitable structure has been difficult.

Making a salt bridge in the circumstance in which the salt solution can be permitted to flow in small quantities across the bridge requires little more than a wick. However, when flow must be restricted to near zero, forces that are otherwise neglected, or are considered on a macro-basis, become important on a micro salt. The need is to maintain an actual, physical liquid-to-liquid contact despite wide ranges in environmental conditions. Surface tension, capillary action, length of the conductive path, shape of the electric field resulting from ion concentration, and other variables that change from instant to instant as a consequence of ion migration, make it difficult to predict and design suitable bridge structures.

SUMMARY OF THE INVENTION

This invention provides yet another salt bridge and ion sensitive electrode structure. It is an object to provide, and it does provide, a structure which exhibits superior performance in practice in a number of commercially important environments.

It is an object to provide a structure whose performance is relatively unaffected by temperature and pressure over a wide range of value of those parameters. A related object is to provide a single design which is useful at any of a wide range of pressure and temperature combinations.

A further object is to provide a design which requires only inexpensive tooling and which is suitable for a wide variety of field applications whereby even those sensors for which there is smaller demand can be produced economically with universal or general purpose components.

Another object is to provide a structure whose performance is uniform in strong magnetic and electric fields in the presence of bubbles and foreign materials notwithstanding rotational orientation.

These and other objects and advantages, which will hereinafter become apparent, are realized, in part, by creating a unit at least the sensor end of which is formed by two concentrically arranged tubular members. The inner tube is available as a reservoir for one body of salt solution, and the annular space between the inner and outer tube, or the region about it, is available for storage of the other body of salt solution. A plug is required at each end of the unit, or at spaced points along its length, so that the solution will be retained. One of those plugs, the one at the sensor end, is made of a material across which a salt bridge will form when placed in contact with a sample solution. The sensing element is fixed to the end of the central tube adjacent to the salt bridge plug.

Thus constructed, the salt bridge plug surrounds the sensor. The effect is that performance is made to be independent of rotational orientation about the axis of the tubes when the unit is placed with the sensor element and the exposed side of the salt bridge plug in contact with the sample liquid. Performance is independent of rotational orientation whether the sample liquid is flowing or includes bubbles or undissolved solids, or is turbulent. Performance is greatly enhanced by forming the plug of porous Teflon.

In the preferred embodiment, the plug has an axial bore into which the inner tubular member is fitted with a tight fit. By that arrangement, the pathway for leakage flow between the reservoir for salt solution and test solution will extend past a limited line (the circumference of the inner tube) and the leakage path can be as long as the plug. The result is that flow of liquid past the salt bridge along the surface of the inner tube is easily prevented, and the degree of tightness with which the plug fits on the inner tube is not critical.

On the other hand, the salt bridge plug has an outside diameter less than the inside diameter of the outer tube in the preferred form. An annular space remains between the plug and the outer tube. In one embodiment, that space is sealed with a single sealing annulus which, by its composition, will not serve as the medium for creation of a salt bridge. In a preferred embodiment, that sealing space contains two spaced sealing annulus', each encompassing the salt bridge plug at an inner circumference and each making sealing engagement at an outer circumference with the inner surface of the outer tube. By that arrangement, the length of the minimum salt bridge path may be made less than the length of the plug and less than the leakage path past the plug at the inner tube wall. Leakage past the outer wall of the salt bridge plug is easier to control than leakage past the inner wall because of the use of the sealing annulus' or O-rings. Therefore, part of the outer surface of the plug above and below the O-rings can be made available as an entry surface for ion migration.

The fact that ions can enter both at the side walls and at the end walls of the salt bridge plug, symetrically about the central axis of the unit, results in an electric and magnetic field pattern and gradient different from what is exhibited in the prior art. That field results from point charges which are in motion and which exist for discrete and random intervals. The exact effect of that configuration cannot be measured at any particular point because measurement would eliminate the point charge, but sensor units configured according to the invention exhibit superior performance — probably as a result of that configuration.

The plug must support a salt bridge in that it must be capable of containing liquid entirely across the bridge. One physical quality that makes that possible is called "porosity." Some polyneric substances, particularily Teflon, can be made in porous form. Teflon, including Teflon-like materials, are the best material thus far discovered, both functionally as a salt bridge vehicle and because it can be fabricated easily. The degree of porosity of Teflon can be controlled and a wide range of porosity is possible.

In a particular form of the invention, juxtaposed grooves are turned in the outer surface of the plug, and in the inner surface of the outer tube, and the O-rings are lodged in those grooves. That plug and O-ring combination are so easily constructed that a preferred embodiment employs that combination at both ends of the electrode unit. The fact that the plug is porous presents no problem at the end of the unit opposite the sensor because it is used in combination with a conventional annular sealing plug at that end. It is customary in the industry to use a double plug at the "cable end" of sensor units.

Again, one advantage of using Teflon plugs and O-ring combinations is that manufacturing dimensions need not be closely held; tolerances need not be "tight," even at the inner diameter of the plug. In applications where the external pressure is substantially higher than internal pressure, inward forcing of the plug is prevented by the inclusion of a simple sleeve extending as a spacer between the two plugs.

In the drawings:

FIG. 1 is a perspective view of an ion sensitive electrode unit which embodies the invention;

FIG. 2 is a cross-sectional view of the unit of FIG. 1 taken on a plane containing its central, longitudinal axis, the inner salt solutions having been omitted for the sake of clarity;

FIG. 3 is an enlarged view of the sensor end of the structure shown in FIG. 2;

FIG. 4 is an elevational view of the sensor end of the unit shown in FIG. 1;

FIG. 5 is a cross-sectional view taken on the central, longitudinal axis of a modified form of sensor unit;

FIG. 6 is a cross-sectional view of the sensor depicted in FIG. 5 taken on a line at 6—6 of FIG. 5; and FIG. 7 is a cross-sectional view of the sensor depicted in FIG. 5 taken on a line at 7—7 of FIG. 5.

DESCRIPTION OF THE PREFERRED EMBODIMENT

The invention is applicable to sensors for detecting any of a number of different ions. It is not limited to any particular structural form, except that at one point along its length, in the vicinity of the point at which ion concentration is measured, the structure consists of a pair of concentrically arranged hollow cylinders, or tubes. The outside diameter of the inner tube is less than the inside diameter of the outer tube so that an annular space remains beween them. That space is sealed with a porous member in which a salt bridge is formed when the unit is placed in service.

While only the sensing end of the unit need comprise the concentric members, it is both convenient and preferred that the inner and outer members comprise elongated tubes arranged concentrically on a common axis and having uniform inner and outer diameters throughout their length. The sensor unit of FIG. 1 employs that construction. The inner tube and the seal are not visible in the drawing. However, the outer tube 10 is visible along with the sensing element 12 at the sensor end of the unit. An electrical cable 14 extends from the other end of the unit where the construction is covered by a boot 16. The upper end 17 of the boot has reduced diameter so that it embraces the cable 14, and the lower end 18 of the boot has larger diameter. It embraces and fits tightly over the upper end of the outer tube 10. The sensor 12 is a bubble formed of pH sensitive glass which is bonded, as shown in FIGS. 2 and 3, to the sensor end of an inner tubular member which, in this case, is simply a glass tube 20. The tube and the bubble are bonded together at the bond region 22.

The outer tubular member may be formed of glass or plastic, or any other inert material. In this embodiment, the outer member, often called the "body" is made of an epoxy material.

The outer diameter of the inner tube 20 is substantially less than the inner diameter of the outer member 10. They are mounted on a common axis so that an annular space is available between the two members. That space is available for use as a container for one body of electrolyte, and the space within the inner tube 20 is available as a container for another body of electrolyte. For that purpose, it is necessary to seal the inner tube at both ends and to seal the annular space between the members at both ends of the unit, or at least at spaced points along the unit. It matters not to the invention how the sealing is accomplished at the cable and boot end of the unit, except that the plug that is employed to seal the annular space between the tubes at the sensor end of the unit can be employed to advantage at the cable and boot end. That will be explained below.

The lower end of the inner tube 20 is sealed with a pH sensitive glass. To sense other ions, that glass would be replaced with a metal, or some other form of, sensor. In any event, the sensor structure would serve to seal the lower, or sensor end, of the inner tube.

It is also necessary both to seal the space between the inner and outer tubular members and to form a salt bridge past that seal. In this embodiment, the same element is employed both in providing and accomplishing both functions. That element is the plug 24. It is formed as an annulus, cylindrical in shape, and having a bore extending through the cylinder on its axis. The diameter of the bore is such that the plug 24 will encompass and embrace the inner tube 20. A sliding fit is adequate. In most applications, the only requirement is that the plug fit tightly enough upon the inner tube so that there is no actual liquid flow past the plug from or into the cavity formed by the annular space between the two tubular elements.

One of the advantages of the invention is that it provides a means for keeping the plug in place notwithstanding that a high pressure differential may be developed across the plug or that it may be subjected to large temperature variations in which the several elements tend to change their physical dimensions. Certainly, the possibility of plug movement can be minimized by close dimensional control and by forming the plug 24 so that it makes a very tight fit on the inner tube. However, that is not essential. In a preferred embodiment, the plug 24 is formed with an outer diameter less than the inner diameter of the outer tubular member 10 whereby an annular space remains between the plug and the outer wall. A sealing annulus, which may have the form of an O-ring, is installed in that annular space. In a preferred form, a retaining groove is formed around the circumference of the plug and a juxtaposed retaining groove is formed around the inner periphery of the outer tube 10. That construction is depicted in several figures of the drawing. Thus, in FIG. 2, an O-ring 26 is shown encompassing the plug 24. The inner circumference of the O-ring is lodged in a retaining groove 28, and the outer circumference of the O-ring is lodged in a groove 30 formed in the inner wall of member 10. It is preferred that two O-rings be used, as shown in FIGS. 2, 3 and 5. In FIG. 2, the second O-ring 32 also encompasses the plug 24 and is lodged in a pair of juxtaposed grooves, one formed around the outer circumference of the plug and the other formed around the inner circumference of the member 10. The O-rings are spaced apart, and, in this embodiment, the lower O-ring 26 encompasses the plug 24 on a plane that is removed an appreciable distance from the plane of the bottom wall 34 of the plug. The use of two O-rings disposed in retaining grooves ensures that the plug 24 will not move despite the application of a substantial pressure differential across the plug.

While the O-rings are important in retaining the plug in position, they have another important function. The plug serves not only as a sealing element; it serves also as the medium in which the salt bridge is formed. It is greatly preferred that the plug be formed of a porous Teflon material. It is required to form a liquid-to-liquid contact within that plug. The electrolytic material from within the sensing unit must penetrate into the plug toward the outer end 24 at the sensor end of the unit. The degree of penetration will depend upon the porosity and the setting characteristics of the plug material, the pressure differential across the plug, and some other factors. The plug material is selected so that the electrolyte does not leak or seep through the plug lest an excessive quantity of salt crystals form on the exposed surface of the plug. When the unit is immersed in a test liquid, some of the test liquid enters into the plug and moves upwardly through the porous Teflon by capillary action until a liquid-to-liquid interface is formed. As temeprature and pressure change, the plane on which that liquid-to-liquid junction is formed tends to move upwardly and downwardly in the plug. It is important that the plug be made of a material that will support that kind of action. The use of the encompassing O-rings provides a means for fixing the length of the salt bridge path at the outer periphery of the plug at something less than the dimension from the top to the bottom of the plug. Considered as a whole, the construction permits a large surface area of contact between the plug and the inner tube to enhance the sealing effect at the inner tube. The average salt bridge path through the plug can be made relatively long. However, the time required for the sample liquid to progress upwardly in the plug to complete the liquid junction is reduced by the fact that the junction path past the O-rings can be made substantially shorter than the overall length of the plug. That, of course, is because test liquid can move upwardly around the outer surface of the plug until it reaches the O-ring. Similarly, the electrolyte material within the unit extends downwardly around the outer periphery of the portion of the plug above the O-ring 32. That construction, in which there is a small annular space around the plug at its sensor end into which test liquid can flow freely but which tends to exclude bubbles and foreign matter, particularly foreign solid matter, from large areas of the plug surface, also tends to ensure unimpeded contact between the plug and the test liquid entirely around the plug wall. This causes insensitivity to external electric and magnetic fields and insensitivity to flow direction of the test liquid. Moreover, the minute fields that are developed as a consequence of individual ion creation and destruction, and which appear as random electrical artifacts, occur entirely around the bridge at the liquid-to-liquid junction. Instead of appearing as noise, their combined effect is simply to provide the junction potential.

Despite superior performance, the structure shown in FIG. 2, and in enlarged form in FIG. 3, is easily manufactured and easily assembled. The effectiveness of that plug and O-ring arrangement, to form a seal against the passage of liquid, warrants its being used as a plug at the cable and boot end of the sensor unit. (As shown in FIGS. 2 and 5.)

As shown in FIG. 2, the second plug is identified by the reference numeral 40. It is used in conjunction with two O-rings 42 and 44, both of which are lodged in juxtaposed pairs of grooves, one formed in the outer periphery of the plug and the other formed in the inner periphery of the body 10. It is not necessary that the plug 40 be formed of Teflon, but it can be formed of that material.

In preferred form, it is used with a back-up plug 46 which, like the plugs of the prior art, is formed of some plastic material which is elastomeric. A similar material is employed inside the inner tube 10 to seal its upper end. That body of elastomeric material is identified in FIG. 2 by the reference numeral 48.

To complete the description, the conductor 14 usually is a coaxial cable. Its center lead 50 is extended down through the plug 48 into the interior of the inner tube 20. The center conductor is usually formed of copper, but it may be plated with another metal. In this case, the conductor 50 is made of silver and a quantity 52 of silver-silver chloride salt material is fixed to its lower end. That salt is immersed in the electrolyte that is contained in the inner tube.

Returning to the upper end of FIG. 2, a silver wire 56 is connected electrically and mechanically to the metal braid shield material 58 of the cable. The silver wire 56 is forced through the plug 46 and the plug 40 down into the annular space between the two tubes. In the finished unit, that space is filled with electrolyte, and the electrolyte is contacted by a quantity 60 of silver-silver chloride material which is fixed to the end of silver wire 56.

The electrolytes were omitted from FIG. 2 for the sake of clarity, but they have been added to FIG. 3 to illustrate that they are, indeed, incorporated in the finished unit.

An alternative structure is shown in FIG. 5. This one is made for severe environmental applications. It differs from the unit shown in FIG. 2 in three respects. First, the outer tubular element, or body, 110 has been notched at 114 at its sensor end. Secondly, the glass sensing unit of FIG. 2 has been replaced with a metallic sensor 112 in FIG. 5. The third difference, one that is related to pressure, is the addition of an inner sleeve 130 within the annular space between the inner and outer tubular members. It serves as a spacer between the upper and lower plugs and serves to transmit forces from one to the other so that forces tending to move the plugs are shared. In this embodiment, that spacer 130 has an outer diameter such that it fits against the inner wall of the outer member. In an alternative construction, the spacer has a smaller diameter and encompasses the inner tube.

Although I have shown and described certain specific embodiments of my invention, I am fully aware that many modifications thereof are possible. My invention, therefore, is not to be restricted except insofar as is necessitated by the prior art.

I claim:

1. An ion sensitive electrode comprising, in combination:
   an outer tubular member having a given inner diameter at a region near one end;
   an inner tubular member assembled concentrically within said one end of outer member and having an outer diameter less than said inner diameter such that an annular space remains between said members;
   bridging and sealing means for sealing said annular space in the region of one end of the assembled members while permitting ionic transfer across the seal;
   the bridging and sealing means comprising an annular plug embracing said inner member and formed of a porous material, said plug having an outer diameter less than the inner diameter of said outer member such that an annular sealing space remains between the plug and said outer member and
   said bridging and sealing means further comprising means in the form of a sealing annulus embracing said plug and bearing against the inner wall of said outer member for sealing said space against the passage of liquid.

2. The invention defined in claim 1 in which the outer wall of said plug and the inner wall of said outer member are each formed with an annular groove juxtaposed to the other and in which said sealing annulus is disposed in said annular groove of the plug and in said annular groove of said inner member.

3. The invention defined in claim 2 in which said plug is formed of a porous polymer of tetrafluoroethylene.

4. The invention defined in claim 2 in which said plug and the inner wall of said outer member are each formed with a pair of spaced grooves, juxtaposed in pairs, and which comprise two sealing annulus' one disposed in each pair of juxtaposed grooves.

5. The invention defined in claim 4 which further comprises a second plug embracing said inner member, a second pair of juxtaposed grooves formed in the outer surface of said second plug and said inner surface of said outer member, and a second pair of sealing annulus' disposed one in each of said second pair of juxtaposed grooves.

6. The invention defined in claim 4 in which said sealing annulus' are formed of a non-porous elastomeric material whereby any fluid path through said porous plug must extend past both of said annulus' in series.

7. The invention defined in claim 6 in which said plug is formed of a porous polymer of tetrafluoroethylene material.

8. An ion sensitive electrode comprising in combination:
   an outer member having a tubular portion of given inner diameter at one end;
   an inner member having a tubular portion whose outer diameter is less than said inner diameter disposed concentrically within the tubular portion of said outer member such that an annular space remains between said portions of said members;
   bridging and sealing means for sealing said annular space while permitting ionic transfer past the seal comprising an annular plug formed of porous polymer of tetrafluoroethylene and disposed in said annular space;
   the outer surface of said plug having a diameter less than the inner diameter of said outer member; and
   which further comprises a non-porous sealing annulus encompassing said outer surface of said plug and bearing against outer member.

9. The invention defined in claim 8 in which the inner wall of said outer member and the outer wall of said plug are formed with annular, juxtaposed grooves in which said sealing annulus is disposed.

* * * * *